United States Patent [19]

Saltzstein et al.

[11] Patent Number: 5,355,892
[45] Date of Patent: Oct. 18, 1994

[54] METHOD AND APPARATUS FOR CONTROLLING A MEDICAL DEVICE WITH A MACRO INSTRUCTION

[75] Inventors: William E. Saltzstein, Amity; Lawrence Hileman; Peter M. Galen, both of McMinnville, all of Oreg.

[73] Assignee: Hewlett-Packard Corporation, Palo Alto, Calif.

[21] Appl. No.: 15,749

[22] Filed: Feb. 10, 1993

[51] Int. Cl.$^5$ .......................................... A61B 5/0432
[52] U.S. Cl. .................................................. 128/710
[58] Field of Search ................. 128/709, 710, 731, 906

[56] References Cited

U.S. PATENT DOCUMENTS

| | | | |
|---|---|---|---|
| 3,058,458 | 10/1962 | Daneman | 128/709 |
| 3,566,370 | 2/1971 | Worthington, Jr. et al. | 128/710 |
| 4,483,346 | 11/1984 | Slavin | 128/710 |
| 4,739,772 | 4/1988 | Hokanson et al. | 128/731 |
| 5,002,062 | 3/1991 | Suzuki | 128/710 |
| 5,086,778 | 2/1992 | Mueller et al. | 128/710 |
| 5,193,541 | 3/1993 | Hatsuwi | 128/906 |
| 5,206,807 | 4/1993 | Hatke et al. | 128/710 |

Primary Examiner—William E. Kamm

[57] ABSTRACT

A cardiograph having a keypad includes an internal disc drive for reading a floppy disc provided to the drive. ROM and RAM in the cardiograph incudes a program for loading a macro instruction contained on a floppy disc into the cardiograph RAM. Another program executes the macro instruction responsive to an operator-actuated input. The macro instruction includes keypad codes which provide patient data and configuration and control instructions to the cardiograph. Several special function codes which do not correspond to keypad codes are provided for pausing the macro instruction, ending the instruction and other special functions. In one aspect, patient data is copied onto the floppy disc from a hospital information system and thereafter provided to the cardiograph preliminary to a cardiographic recording session with the patient.

7 Claims, 4 Drawing Sheets

METHOD AND APPARATUS FOR CONTROLLING A MEDICAL DEVICE WITH A MACRO INSTRUCTION

BACKGROUND OF THE INVENTION

1. Field of the Invention

The present invention relates generally to medical testing devices of the type having a keypad for providing instructions and data to the device and more particularly to methods and apparatus for controlling such devices.

2. Description of the Related Art

A variety of medical devices used to obtain patient data include a keypad for providing instructions and data to the device. One such device is a cardiograph which is connected to a patient via a plurality of electrodes. The cardiograph electrodes detect electrical activity resulting from the patient's heart across different selected pairs of the electrodes thereby providing ECG waveforms to the cardiograph. A typical cardiograph is equipped with a memory for storing patient waveforms, a screen for displaying the waveforms as they occur and a printer for printing the waveforms on paper.

Such cardiographs also typically include a keypad which an operator uses to perform a number of different functions. At each cardiographic recording session, patient data including the patient's name, room number (if in a hospital) and patient ID number may be entered. Data such as age, race, weight, blood pressure, operator identity, patient medication, etc. may also be entered. The name of the physician requesting the cardiographic examination also is usually included.

In addition to keying in data such as that described above, cardiograph operators must provide instructions via the keypad which control the cardiograph during the process of obtaining and analyzing ECG waveforms. For example, instructions must be provided concerning which pairs of electrodes, referred to as leads, are selected to be recorded. The duration of the recorded waveform must also be selected. Sometimes data is obtained for preselected periods alternating with a period during which no data is recorded in order to observe changes in the waveform over time.

Often different physicians provide standing instructions concerning configuration of the cardiograph for substantially all cardiographic recording sessions, e.g., duration of recording, selection of leads for recording, the order in which the different leads are recorded, etc. Thus, an operator of the cardiograph may provide some of the instructions to configure the cardiograph based on the requesting physicians standing orders.

Cardiographic recording is typically done in a hospital by an ECG technician who uses a cardiograph mounted on a cart. The technician typically begins a round by obtaining a list of patients, their room numbers and the physician requesting each cardiogram. The list may include information concerning the time of day when the session is to occur and the type of data, e.g., which leads are to be recorded, etc., that the requesting physician would like. The technician then takes the list and the cardiograph and proceeds to the first room. Once there, the technician connects the electrodes to the patient and begins keying information into the cardiograph via the keypad. This information includes patient identifying data such as that described above.

Thereafter, the technician configures the cardiograph with operating instructions which cause it to take selected leads for selected durations as described above. As mentioned above, some of the instructions provided by the technician via the keypad may not appear on the list of patients and related instructions but rather may be based upon standing orders issued by the requesting physician. Once complete, the technician disconnects the electrodes and takes the cardiograph to the next patient for the next recording session.

The main cause of error in obtaining cardiographic data as described above results from mistakes made by the technician when patient data and cardiograph configuration and control data is entered by the technician via the keypad. Such mistakes result in typographical errors in the data associated with the particular cardiogram and may even result in misidentification of a patient as a result of an error in entry of a room number or patient identification number. Similarly, when the keypad is used to provide cardiograph configuration and control commands, errors can result in acquiring data other than that requested.

It would be desirable to eliminate or substantially reduce entry of patient data and configuration and control commands to devices, such as a cardiograph, which obtain and analyze data from a patient.

SUMMARY OF THE INVENTION

The present invention comprises a method for using a medical testing device of the type having a keypad for providing instructions and data to the device responsive to operator actuation of switches on the keypad. A macro instruction is generated which initiates a plurality of signals simulating actuation of switches on the keypad in a predetermined order. The macro instruction is stored on a magnetic disc or the like which is thereafter engaged with the testing device. Transducers are arranged for collecting patient data and the macro instruction is executed.

In another aspect of the invention, a medical testing device includes a transducer for collecting patient data. The device also includes means for displaying information relating to the data and a processor for controlling the collection and display of the data. A memory in the device stores processor instructions and data. The memory and processor are operatively connected to a keypad which provides instructions and data responsive to operator actuation of switches on the keypad. A magnetic disc or the like is readable by a reading device such as a disc drive. A macro instruction for initiating a plurality of signals simulating actuation of switches on the keypad in a predetermined order is stored on the magnetic disc. Means are providing for executing the macro instruction on the disc responsive to an operator-generated signal.

In another aspect of the invention, patient data and cardiograph configuration and control information are contained in a macro instruction stored on a magnetic disc which is inserted into a cardiograph by an operator thereof who thereafter executes the macro instruction.

It is a general object of the present invention to provide a method and apparatus for controlling a medical device with a macro instruction which overcomes the above-enumerated disadvantages associated with the prior art.

It is another object of the present invention to provide patient data and cardiographic configuration and control instructions via a macro instruction which is provided to a cardiograph.

The foregoing and other objects, features and advantages of the invention will become more readily apparent from the following derailed description of a preferred embodiment which proceeds with reference to the drawings.

DETAILED DESCRIPTION OF THE PREFERRED EMBODIMENT

Figure 1:
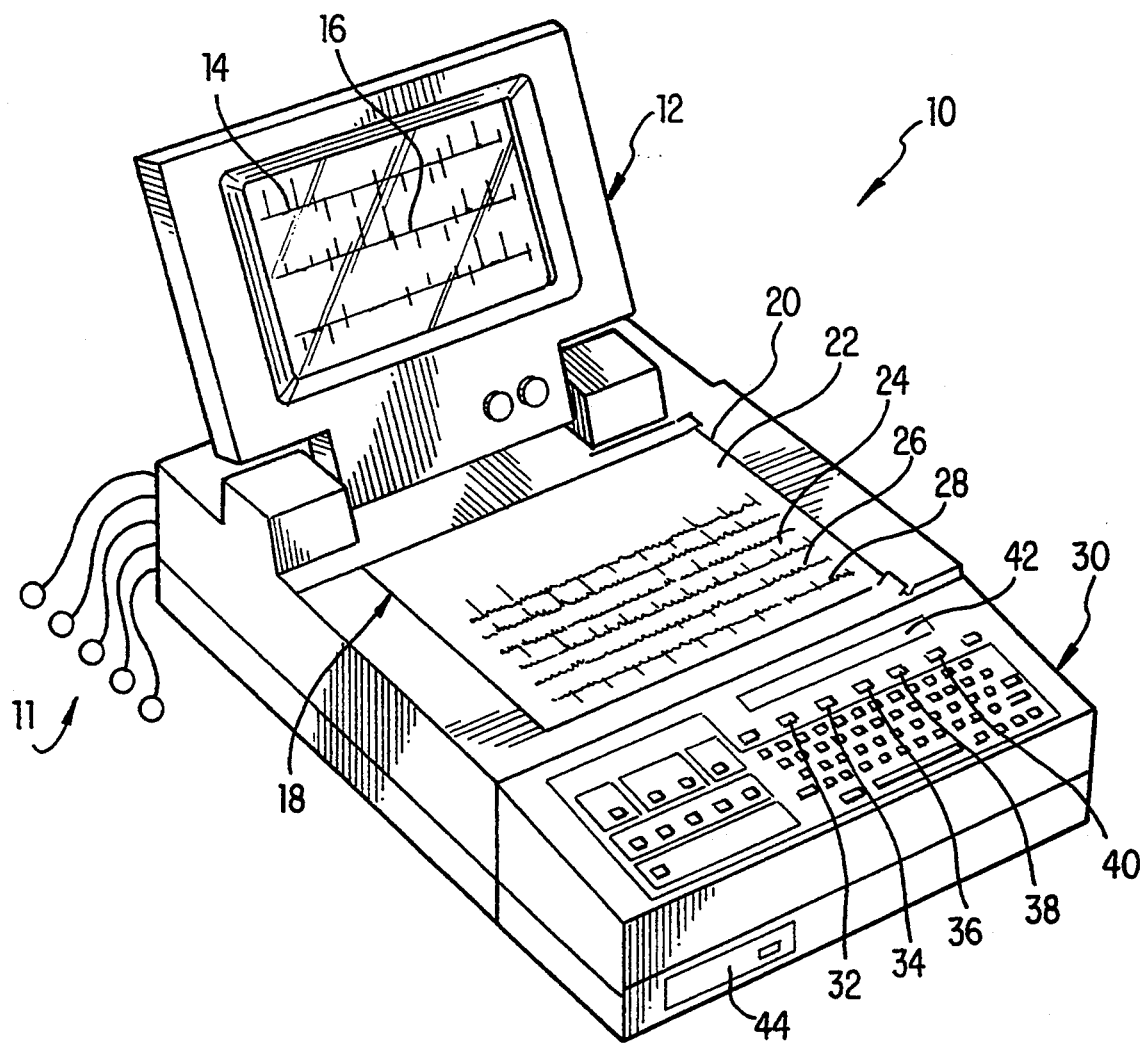
FIG. 1 is a perspective view of a cardiograph constructed in accordance with the present invention.

Turning now to FIG. 1, indicated generally at 10 is a cardiograph constructed in accordance with the present invention. The cardiograph includes a flat-panel display screen 12 upon which ECG waveforms, like waveforms 14, 16, are displayed. These ECG waveforms are generated by detecting electrical activity resulting from the patient's heart via a plurality of electrodes 11 which are coupled to cardiograph 10. Cardiograph 10 further includes an internal printer and a pad of cardiograph recording paper, also received internally of cardiograph 10. In FIG. 1, a chart 18 is printed on an end of the roll of paper which emerges from cardiograph 10 via a slot 20. Chart 18 includes an upper portion 22 upon which various patient data and information relating to the configuration of the cardiograph is printed. A lower portion 24 of chart 18 includes a background grid and has ECG waveforms, like waveforms 26, 28 printed thereon. Indicated generally at 30 is a keypad which includes a plurality of keys for providing instructions and data to the cardiograph via a different switch controlled by each key. The keypad is operatively connected to a digital processor 13, to random access memory(RAM), and to a read-only memory (ROM) which contains computer code for controlling cardiograph functions via the processor. The processor, RAM and ROM are all located within cardiograph 10.

Included in keypad 30 are function keys 32, 34, 36, 38, 40, each of which includes an assigned identifier F1, F2, F3, F4, F5, respectively. Each of the function keys is positioned beneath a display 42 which provides an alphanumeric indication above each key that indicates the function performed when the associated key is depressed. The functions assigned to each key can vary depending on the mode on which the cardiograph is operating.

Cardiograph 10 includes a slot 44 for receiving a 3½" floppy disc into a disc drive 45 internal to cardiograph 10.

Figure 2:
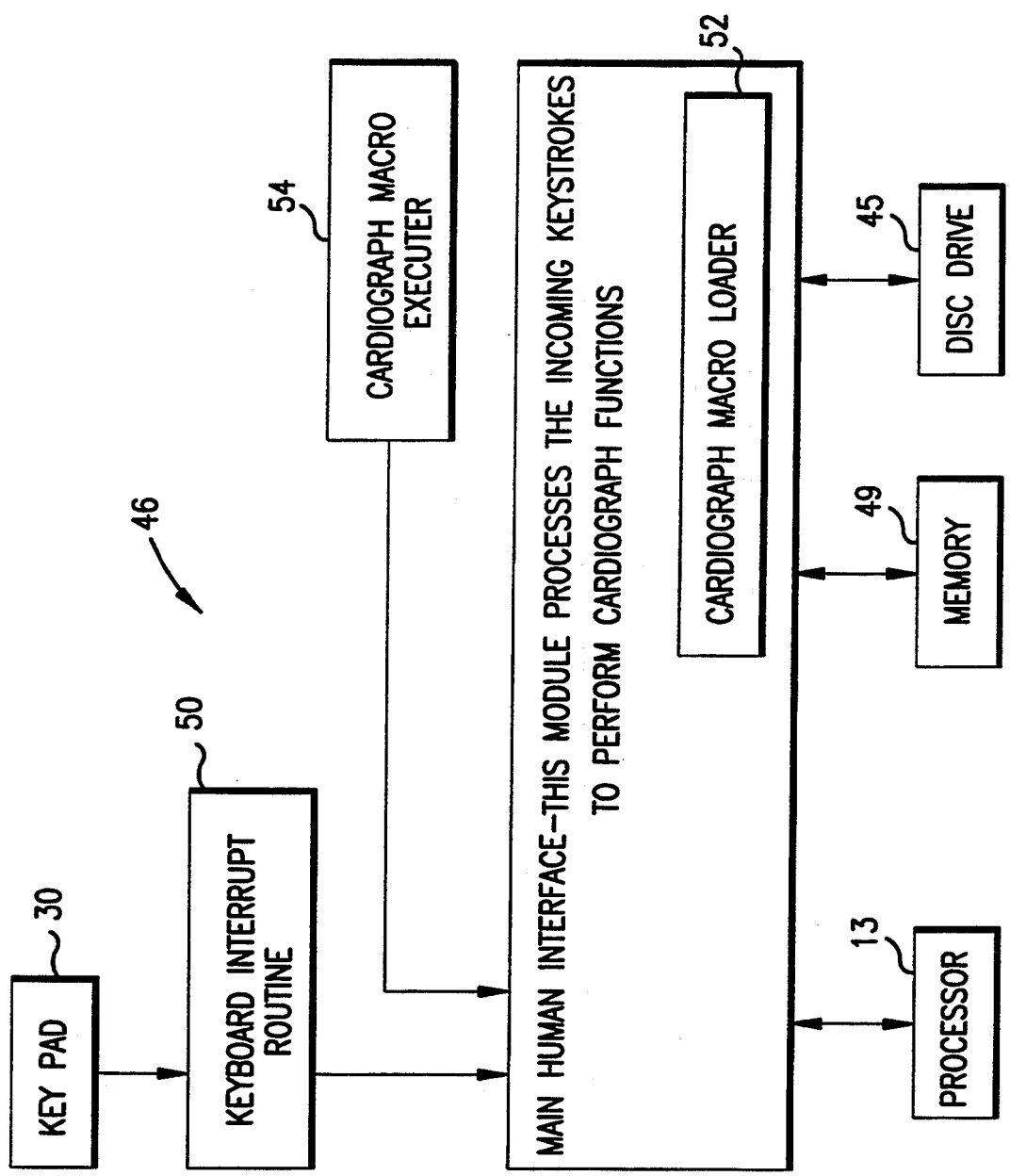
FIG. 2 is a block diagram of a portion of the cardiograph of FIG. 1.

Turning now to FIG. 2, indicated generally at 46 is a block diagram indicating a portion of the internal structure of cardiograph 10. Included therein is module 48 which receives coded information via a keyboard interrupt routine 50 indicating which keys on keypad 30 are depressed by an operator. Module 48 in turn provides signals to other portions (not shown in FIG. 2) of the cardiograph for providing configuration and control signals and data responsive to input at keypad 30.

Module 48 includes a cardiograph macro loader program 52 which loads a selected macro instruction, as will be hereinafter described from disc drive 45, into memory 49, which includes both RAM and ROM, in the cardiograph. A cardiograph macro executor program 54 executes a loaded macro instruction in a manner which is also further described.

Prior to describing operation of loader program 52 and executor program 54, consideration will first be given to the form in which each macro instruction is provided to the cardiograph. The macro instructions are contained on a standard 3½" floppy disc which is inserted into slot 44 (in FIG. 1) on the cardiograph and read by the internal disc drive 45. In the present embodiment, the disc includes a directory called MACRO. The MACRO directory has a plurality of subdirectories thereunder, each of which contains macro instructions. For example, one subdirectory is called PATIENTS. Included therein is a single MACRO.LST file and a plurality of macro instruction files each of which relates to a different patient. For a subdirectory having, e.g., 35 patient files, the files contained in \ MACRO \ PATIENTS are as follows:

TABLE 1

MACRO.LST
PAT0001.MAC
PAT002.MAC
PAT003.MAC
PAT004.MAC
PAT005.MAC
.
.
PAT035.MAC

Each of the patient files, i.e. those appearing beneath the MACRO.LST in the above chart, includes an attribute field of 70 bytes and a keystrokes field of 1968 bytes. The attribute field contains a list of attributes, such things also referred to herein as identifiers, associated with each patient file such as a patient name, patient identification number, room number or department (in a hospital). Each attribute is separated from the next by a comma. The keystrokes field contains key codes which are provided by cardiograph macro executor 54 (in FIG. 2) to module 48. Thus, when a macro instruction is executed, key codes are rapidly provided to module 48 and have the same effect as if provided through keypad 30 via keypad interrupt routine 50. Thus, patient data and cardiographic control and configuration information is provided.

The keystroke codes provided from the macro instruction include codes for all of the punctuation appearing on the keypad, lower and upper case letters, function numbers, keyboard return and other control functions on the keyboard. In addition, codes are provided to effect control functions which do not have corresponding keystroke combinations at the keypad such as wait for enter, execute at, write at, no op, chain, etc. Where an address is required, for example in an execute at command, a four-byte hex address must be included in the macro instruction. Where a count is required such as in wait for —— (seconds), the number is provided in a single hex byte.

The MACRO.LST file consists of a 70-byte template field which includes the generic names for each of the attributes appearing in the attribute field of each of the patient files. Thus, the template field for the MAC- RO.LST file in the PATIENTS subdirectory is as follows: NAME, PATIENT ID, ROOM NUMBER, DEPARTMENT. After the 70-byte template field, there is a plurality of 93-byte fields which each correspond to a different patient file in the PATIENTS subdirectory. The first 70 bytes in each field includes the attributes set forth in the template field, namely the name of the particular patient, that patient's ID number, room number and department. The next 10 bytes comprises a flag field which has one of two conditions, namely flagged or unflagged. The last field comprises a 13-byte field containing the name of the corresponding patient file (as shown in Table 1 above) in the PATIENTS subdirectory.

In addition to the PATIENTS subdirectory, there may be other subdirectories contained on the floppy disc which contain macro instructions, for example there could be a DOCTORS subdirectory which provides data and instructions for configuring and controlling the operation of the cardiograph based upon a different doctor's standing instructions. As with the patient's subdirectory, the DOCTORS subdirectory includes a MACRO.LST file plus a plurality of files containing macro instructions each of which is associated with a different doctor. There can also be, e.g., a TESTS subdirectory which contains a different macro instruction file associated with a particular kind of test. Again, the TESTS subdirectory contains a MACRO.LST file as described above. When a particular test is selected from the TESTS subdirectory, the cardiograph is configured to perform the selected tests.

Figure 3:
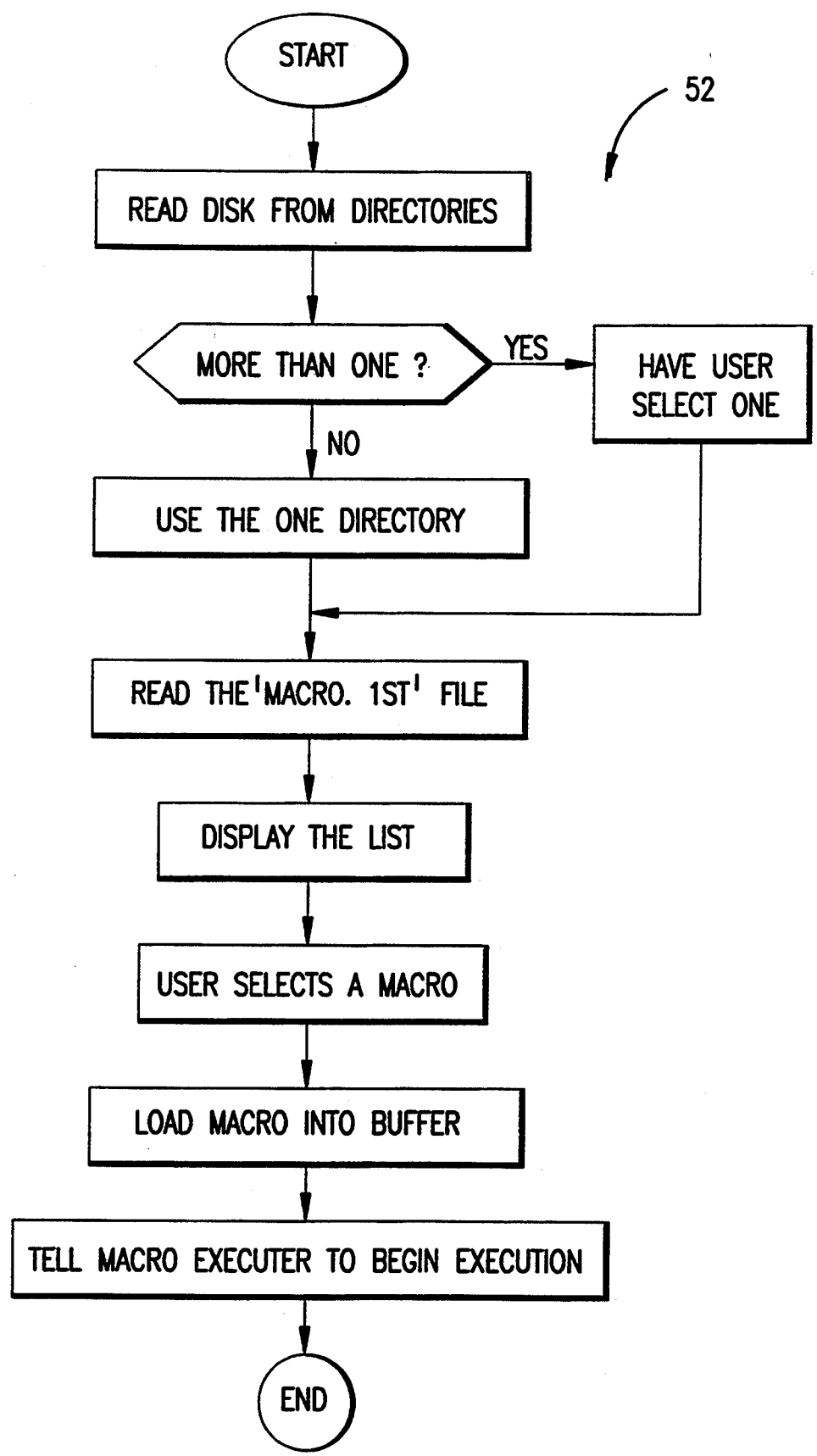
FIG. 3 is a flow chart of one computer program shown in FIG. 2.

Turning now to FIG. 3, consideration will be given to the manner in which an operator uses cardiograph 10. First, an operator inserts a floppy disc in slot 44 of the cardiograph. Next, the cardiograph is placed into a mode for selecting a macro instruction by pressing a predetermined key combination, namely ALT and ID. This starts the macro loader as indicated in chart 52, which then reads the disc for subdirectories under the /MACRO directory. Again, with reference to chart 52, if there is more than one subdirectory, a list is displayed on the screen and the functions of SELECT, NEXT, and PREVIOUS are assigned to function buttons 32, 34, 36, respectively. A highlight bar appears on the screen on the name of a single subdirectory. The bar is moved by using the NEXT and PREVIOUS functions until the desired directory is highlighted as which point the select button is depressed. This causes program 52 to read the MACRO.LST file and display the list. Assuming in the present example that the PATIENTS subdirectory is selected, the list appearing on the MACRO.LST file is displayed. An example of such a display is shown in the following table:

TABLE 2

| Name | ID No. | Room No. | Dept. |
|---|---|---|---|
| ANDERSON, M. | 52178 | 326 | PED |
| BLAKE, T. | 46032 | 482 | MAT |
| DAVIS, L. | 89173 | 601 | CC |
| JONES, A. | 45022 | 232 | WING A |
| MORRIS, B. | 37911 | 344 | PED |
| THOMAS, L. | 42368 | 322 | PED |
| SMITH, S. | 67409 | 417 | MAT |
| WEIDNER, T. | 98217 | 501 | WING B |

As the above table is displayed, the program assigns the following functions to keys 32, 34, 36, 38: SELECT, SORT, NEXT, PREVIOUS. As is the case with the list of subdirectories, the highlight bar highlights the data on one of the lines in the above table. The name of the highlighted file appears on the top line of display 42 with the four functions assigned to each of the first four function keys appearing on the second line and above the key associated therewith. If the operator would like to sort the list into a different order, button 34, SORT, is depressed. This causes the attribute names in the template field on the MACRO.LST to be displayed above an associated one of function keys 32-40, i.e., NAME, PATIENT ID, ROOM NUMBER, DEPARTMENT. The operator then selects one of the attributes for sorting by depressing the associated function key. The program then sorts each line of information as is set forth in Table 2 above into ASCII order. In other words, if NAMES is selected, each line is placed in alphabetical order by patient name as set forth in the chart above. If, however, ROOM NUMBER, is selected, the information in each line remains in the order as shown in Table 2 but the vertical listing of the lines is shifted into ascending room number. Similarly, sorts can be done by selecting PATIENT ID or DEPARTMENT.

After the operator sorts the list as desired, a patient is selected by pressing the function key associated with the SELECT function (when the desired line is highlighted). This causes program 52 to load the file named on MACRO.LST which is associated with (but not displayed) the selected line of patient information. The selected macro instruction is then loaded into a buffer and execution of program 54 starts.

Figure 4:
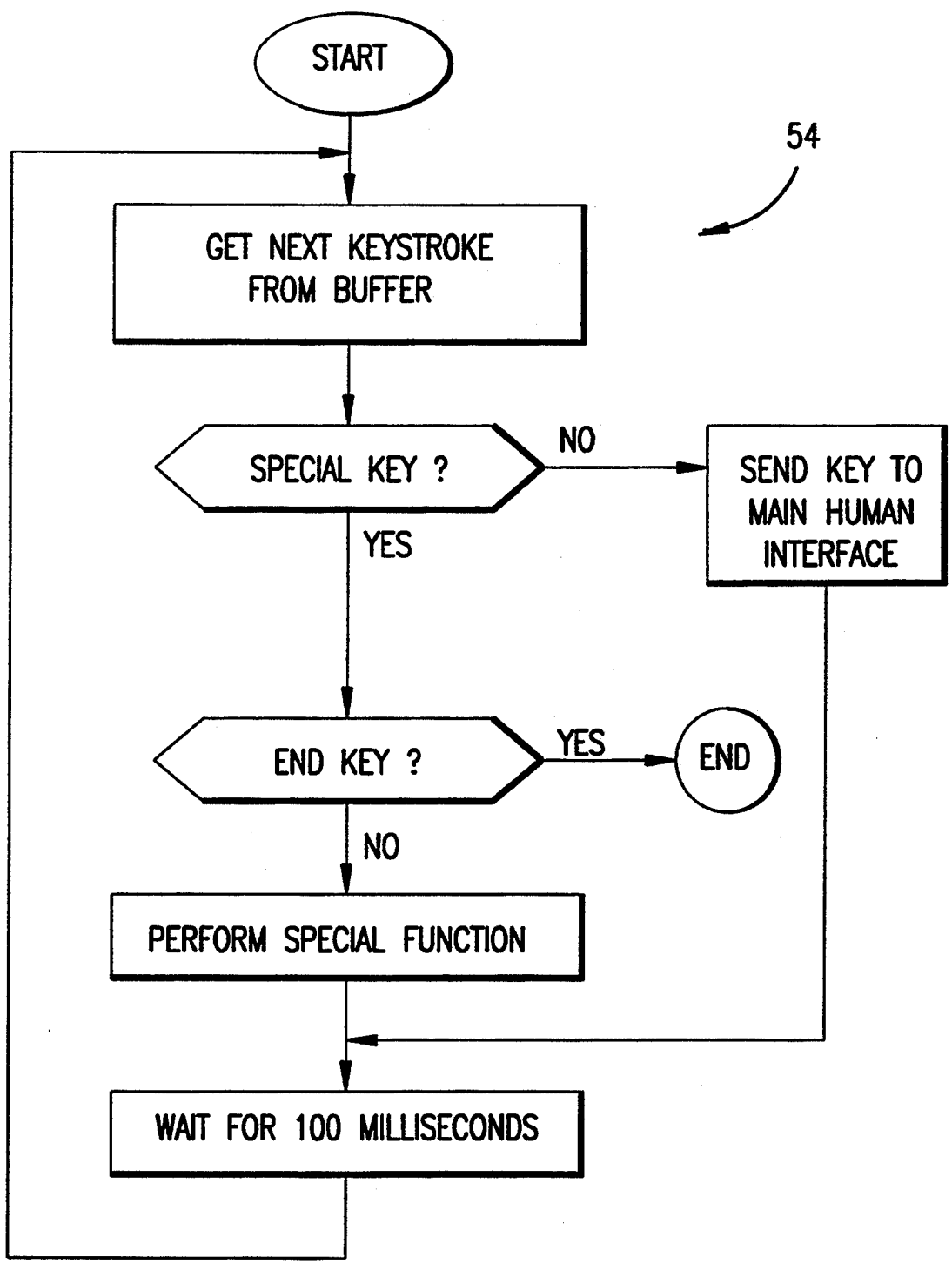
FIG. 4 is a flow chart of another computer program shown in FIG. 2.

Turning now to FIG. 4, program 54 gets the first keystroke in the 1968-byte field in the selected macro instruction file. If it is not one of the pseudo-keys described above, i.e., one having a code for performing a special function that does not correspond to a keyboard key or key combination, program 54 sends the key code to module 48. There is then a 100-millisecond pause, and the next keystroke is obtained from the buffer. In the event that one of the special function codes is selected, program 54 checks to see whether or not it is the end of the macro instruction. If not, the special function is performed, such as (a) an interruption of execution of the macro instruction to permit the operator to enter data or (b) a chain to another macro instruction, there is a 100-millisecond wait, and the next keystroke is obtained from the buffer.

In the event that the end key is detected, a flag is generated and the flag field on the MACRO.LST file is changed to indicate a flagged condition. This results in an exclamation point appearing at the beginning of the line on the display associated with the file which was flagged. It also shifts the line into a lower portion of the display where all flagged files are grouped and maintained in sorted order within the flagged files as indicated by the following revision of Table 2:

TABLE 3

| Name | ID No. | Room No. | Dept. |
|---|---|---|---|
| ANDERSON, M. | 52178 | 326 | PED |
| DAVIS, L. | 89173 | 601 | CC |
| JONES, A. | 45022 | 232 | WING A |
| SMITH, S. | 67409 | 417 | MAT |
| WEIDNER, T. | 98217 | 501 | WING B |
| !BLAKE, T. | 46032 | 482 | MAT |
| !MORRIS, B. | 37911 | 344 | PED |
| !THOMAS, L. | 42368 | 322 | PED |

Thus, each time the operator runs a particular patient macro, it is flagged and sorted to the bottom of the screen to enable the operator to track which patients have been completed. So flagging a particular line does not prevent an operator from again selecting the line and rerunning the macro instruction contained in the associated patient file; it simply provides a visual indication of which macro instructions have been previously run.

In many hospitals, patient and other administrative information is tracked on information systems. Thus, much of the identifying patient data,, including name, ID number, room number, department and other information is contained in the information system. This information can therefore be taken directly from the information system and with only a small amount of formatting, which is appreciable to a person having ordinary skill in the art, can be placed in condition for execution as a macro instruction. A person having ordinary skill in the art can write a computer program for constructing the .MAC files given the patient identification data and the instructions and configurations desired for the cardiograph. In addition to the above-described uses for macro instructions, cardiograph functionality can also be upgraded using a macro instruction. In other words, the code contained internal to the cardiograph which programs the processor to control various functions can be modified by running a macro instruction which updates or revises the current code. It should be appreciated that the present invention may be applied to any medical testing device which utilizes a keypad and which detects and analyzes data either directly from a patient or by analyzing blood, urine or the like from a particular patient.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

We claim:

1. A method for enhanced efficiency in the utilization of a cardiograph which includes a digital processor, memory and a keypad which includes a plurality of keys for providing instructions and data to said cardiograph which relate to collection and display of cardiographic data, said method comprising the steps of:

providing a macro instruction for initiating a plurality of signals which simulate actuation of said plurality of keys in a predetermined order for providing instruction and data relating to collection and display of cardiographic data for a selected patient;

storing said macro instruction within portable storage media;

temporarily coupling said portable storage media to said digital processor;

connecting said cardiograph to said selected patient;

initiating execution of said macro instruction; and collecting cardiographic data for said selected patient in response to execution of said macro instruction.

2. The method for enhanced efficiency in the utilization of a cardiograph according to claim 1, further including the steps of:

providing a plurality of macro instructions, each of said plurality of macro instructions for initiating a plurality of signals which simulate actuation of said plurality of keys in a predetermined order for providing instruction and data relating to collection and display of cardiographic data for an associated patient;

storing said plurality of macro instructions within portable storage media;

selecting a particular one of said plurality of macro instructions;

initiating execution of said particular one of said macro instructions; and collecting cardiographic data for a selected patient associated with said particular one of said plurality of macro instructions in response to execution of said particular one of said plurality of macro instructions.

3. The method for enhanced efficiency in the utilization of a cardiograph according to claim 2, further including the step of generating an indication to an operator of said cardiograph that said particular one of said plurality of macro instructions has been executed.

4. The method for enhanced efficiency in the utilization of a cardiograph according to claim 2, wherein said cardiograph includes a display and wherein said method further includes the step of displaying each macro instruction and particular data for an associated patient.

5. The method for enhanced efficiency in the utilization of a cardiograph according to claim 2, wherein each of said plurality of macro instructions is associated with a plurality of attributes and wherein said method further includes the step of sorting said plurality of macro instructions by a selected attribute prior to said step of selecting a particular one of said plurality of macro instructions.

6. A medical testing device comprising:

at least one transducer for collecting patient data;

a display;

a processor coupled to said at least one transducer and said display for controlling the collection and display of data;

a memory device coupled to said processor for storing said processor instructions and data;

a keypad having a plurality of keys operatively coupled to said processor and said memory device for providing instructions and data thereto in response to operator actuation of said plurality of keys;

a disc drive unit operatively connected to said processor and said memory device;

a storage disc adapted to be inserted within said disc drive unit, said storage disc including a macro instruction for initiating a plurality of signals which simulate actuation of said plurality of keys in a predetermined order for providing instruction and data relating to collection and display of data for a selected patient;

means for initiating execution of said macro instruction in response to an operator generated signal.

7. The medical testing device according to claim 6, wherein said at least one transducer comprises a plurality of electrodes for detecting electrical activity resulting from a patient's heart.

* * * * *